(12) United States Patent
Ho

(10) Patent No.: US 9,919,120 B2
(45) Date of Patent: Mar. 20, 2018

(54) RESPIRATORY INTERFACE DEVICE WITH FLEXIBLE COVER

(75) Inventor: Peter Chi Fai Ho, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1104 days.

(21) Appl. No.: 13/132,453

(22) PCT Filed: Nov. 21, 2009

(86) PCT No.: PCT/IB2009/055260
§ 371 (c)(1),
(2), (4) Date: Jun. 2, 2011

(87) PCT Pub. No.: WO2010/073138
PCT Pub. Date: Jul. 1, 2010

(65) Prior Publication Data
US 2011/0247628 A1   Oct. 13, 2011

Related U.S. Application Data

(60) Provisional application No. 61/139,713, filed on Dec. 22, 2008.

(51) Int. Cl.
*A61M 16/06* (2006.01)
*A61M 16/08* (2006.01)
(Continued)

(52) U.S. Cl.
CPC ........ *A61M 16/06* (2013.01); *A61M 16/0605* (2014.02); *B29C 45/1676* (2013.01);
(Continued)

(58) Field of Classification Search
CPC .. A61M 16/06; A61M 16/10; A61M 16/0683; A61M 16/0605; A61M 16/0638;
(Continued)

(56) References Cited

U.S. PATENT DOCUMENTS

| 1,878,464 A | * | 9/1932 | Bulmer | ................. A61M 16/06 |
| | | | | 128/205.25 |
| 2,307,730 A | * | 1/1943 | Heribert | ................. A62B 18/02 |
| | | | | 128/207.12 |

(Continued)

FOREIGN PATENT DOCUMENTS

| GB | 150232 A | * | 9/1920 | ............. A62B 18/08 |
| GB | 438863 A | * | 11/1935 | ......... A41D 13/1146 |

(Continued)

OTHER PUBLICATIONS

MedGraphics preVent Pneumotach, Dec. 7, 2004 http://www.medgraphics.com/datasheet_preVent.html.

*Primary Examiner* — Kathryn E Ditmer
(74) *Attorney, Agent, or Firm* — Michael W. Haas

(57) ABSTRACT

The present invention is relating to various embodiments of a respiratory interface device, such as a mask, that includes a fabric body structured to accommodate one or both of a nasal and oral region of a user's face. The fabric body includes a fabric connecting member extending therefrom structured to receive a coupling device for delivering a gas to the respiratory interface device. In another embodiment, the fabric body includes a non-fabric support element.

12 Claims, 6 Drawing Sheets

(51) Int. Cl.
*B29C 45/16* (2006.01)
*A61M 16/10* (2006.01)

(52) U.S. Cl.
CPC ..... *A61M 16/0683* (2013.01); *A61M 16/0825* (2014.02); *A61M 16/10* (2013.01); *A61M 2210/0618* (2013.01)

(58) Field of Classification Search
CPC .............. A61M 16/08; A61M 16/0816; A61M 16/0875; B29C 45/1676
USPC ...... 128/206.28, 19, 206.12, 206.13, 206.16, 128/206.19, 206.18, 206.21, 206.27, 128/207.13, 207.11
See application file for complete search history.

(56) References Cited

U.S. PATENT DOCUMENTS

| | | | | |
|---|---|---|---|---|
| 2,921,581 A * | 1/1960 | Swearingen | ........... | A62B 18/00 128/206.25 |
| 3,130,722 A * | 4/1964 | Dempsey | ........... | A41D 13/1146 128/206.28 |
| 3,695,264 A * | 10/1972 | Laeral | ............... | A61M 16/0683 128/202.28 |
| 5,857,460 A * | 1/1999 | Popitz | ................... | A61M 16/06 128/204.22 |
| 5,884,336 A * | 3/1999 | Stout | ...................... | A62B 9/003 128/205.27 |
| 5,918,598 A * | 7/1999 | Belfer | ................ | A41D 13/1176 128/205.25 |
| 6,016,804 A * | 1/2000 | Gleason | ................. | A62B 18/10 128/205.25 |
| 6,102,039 A | 8/2000 | Springett | | |
| 6,272,690 B1 * | 8/2001 | Carey | ..................... | A41D 13/11 2/171 |
| 6,357,440 B1 * | 3/2002 | Hansen et al. | ........... | 128/206.19 |
| 8,439,038 B2 * | 5/2013 | Steindorf et al. | ........ | 128/206.15 |
| 2002/0023647 A1 * | 2/2002 | Hansen | ................. | A61M 16/06 128/205.25 |
| 2002/0162556 A1 * | 11/2002 | Smith | .................... | A61B 5/087 128/207.12 |
| 2005/0098183 A1 | 5/2005 | Nash | | |
| 2005/0199240 A1 * | 9/2005 | Hall | ........................ | 128/206.26 |
| 2005/0252839 A1 * | 11/2005 | Curran et al. | ................ | 210/138 |
| 2005/0284481 A1 | 12/2005 | Meyer | | |
| 2006/0102184 A1 | 5/2006 | Kullik | | |
| 2006/0199457 A1 * | 9/2006 | Hall et al. | ..................... | 442/327 |
| 2008/0142015 A1 * | 6/2008 | Groll | ........................ | 128/206.24 |
| 2008/0168991 A1 * | 7/2008 | Eifler et al. | ............. | 128/205.25 |
| 2008/0276938 A1 * | 11/2008 | Jeppesen | ........... | A61M 16/0666 128/204.18 |
| 2009/0065005 A1 * | 3/2009 | Ades | .................... | A61M 16/06 128/205.25 |
| 2009/0320848 A1 * | 12/2009 | Steindorf | ............. | A62B 23/025 128/206.21 |

FOREIGN PATENT DOCUMENTS

| | | |
|---|---|---|
| GB | 2397244 A | 7/2004 |
| GB | 2397244 A1 | 7/2004 |
| JP | H05177006 A | 7/1993 |
| JP | 2000312724 A | 11/2000 |
| JP | 2002505607 A | 2/2002 |
| JP | 2005304574 A | 11/2005 |
| JP | 2011519284 A | 7/2011 |
| WO | WO0076568 A1 | 12/2000 |
| WO | WO2005004963 A2 | 1/2005 |
| WO | WO2007109837 A1 | 10/2007 |
| WO | WO2007120355 A2 | 10/2007 |
| WO | WO2009108994 A1 | 9/2009 |

* cited by examiner

RESPIRATORY INTERFACE DEVICE WITH FLEXIBLE COVER

CROSS-REFERENCE TO RELATED APPLICATIONS

This patent application claims the priority benefit under 35 U.S.C. § 119(e) of U.S. Provisional Application No. 61/139,713 filed on Dec. 22, 2008, the contents of which are herein incorporated by reference.

BACKGROUND OF THE INVENTION

1. Field of the Invention

The present invention relates to respiratory interface devices for transporting a gas to and/or from an airway of a user, and in particular, to respiratory interface devices, such as masks, that include a fabric body constructed of a fabric material.

2. Description of the Related Art

A variety of respiratory masks are known which contact the areas surrounding the nose and/or mouth of a human user and that are designed to create an effective fit against the user's face. Typically, gases can be provided at a positive pressure within the mask for consumption by the user. The uses for such masks include high altitude breathing (aviation applications), swimming, mining, fire fighting and various medical diagnostic and therapeutic applications.

One requisite of many of these masks, (e.g.) particularly medical respiratory masks, is that they provide an effective fit against the user's face and that the mask contours with the user's face to limit or prevent leakage of the gas being supplied. Commonly, in conventional mask configurations, an effective mask-to-face fit has been attained in many instances only with considerable discomfort for the user. This problem is most crucial in those applications, especially medical applications, which require the user to wear the mask continuously for hours or perhaps even days. In such situations, the user often will not tolerate the mask for long durations and therefore optimum therapeutic or diagnostic objectives will not be achieved, or will be achieved with great difficulty and considerable user discomfort.

Several types of respiratory masks for the types of applications mentioned above are known. Perhaps the most common type of mask incorporates a substantially rigid structure such as a faceplate to support the more flexible sealing member which comes into contact with the user's face, such as a back cushion portion. The rigid structure of the faceplate restricts or limits the ability of the cushion portion to conform to the facial contours of the user. If the fit is not effective, there will be gaps in the mask-to-face interface resulting in gas leaking from the mask at the gaps.

Considerable force will be required to compress the mask member to close the gaps and attain a satisfactory seal in those areas where the gaps occur. Typically, this required force will be provided by straps that are connected to the mask to securely fit the mask to the face of the user. Such force is undesirable because it produces high pressure points elsewhere on the face of the user where the mask contour is forcibly deformed against the face to conform to the user's facial contours. This will produce considerable user discomfort and possible skin irritation and breakdown anywhere the applied force exceeds the local perfusion pressure, which is the pressure that is sufficient to cut off surface blood flow. Thus, it would be desirable to minimize or eliminate the rigid structure of the mask to improve the ability of the cushion portion to conform to the facial contours of the user and therefore to enhance the fit of the mask to the user's face.

SUMMARY OF THE INVENTION

Accordingly, it is an object of the present invention to provide a respiratory interface device that overcomes the shortcomings of conventional respiratory interface devices. This object is achieved according to one embodiment of the present invention by providing a respiratory interface device that includes a fabric body structured to accommodate one or both of a nasal and oral region of a user's face, the fabric body having an opening formed therein; and a fabric connecting member extending outwardly from the fabric body, the fabric connecting member extending along the periphery of the opening, the fabric connecting member being structured to receive a coupling device for delivering a gas to the respiratory interface device.

In another embodiment, the invention provides a respiratory interface device which includes a fabric body structured to accommodate one or both of a nasal and oral region of a user's face, the fabric body having an opening formed therein; the opening being structured to receive a coupling device for delivering a gas to the respiratory interface device; and at least one non-fabric support element coupled to the fabric body.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
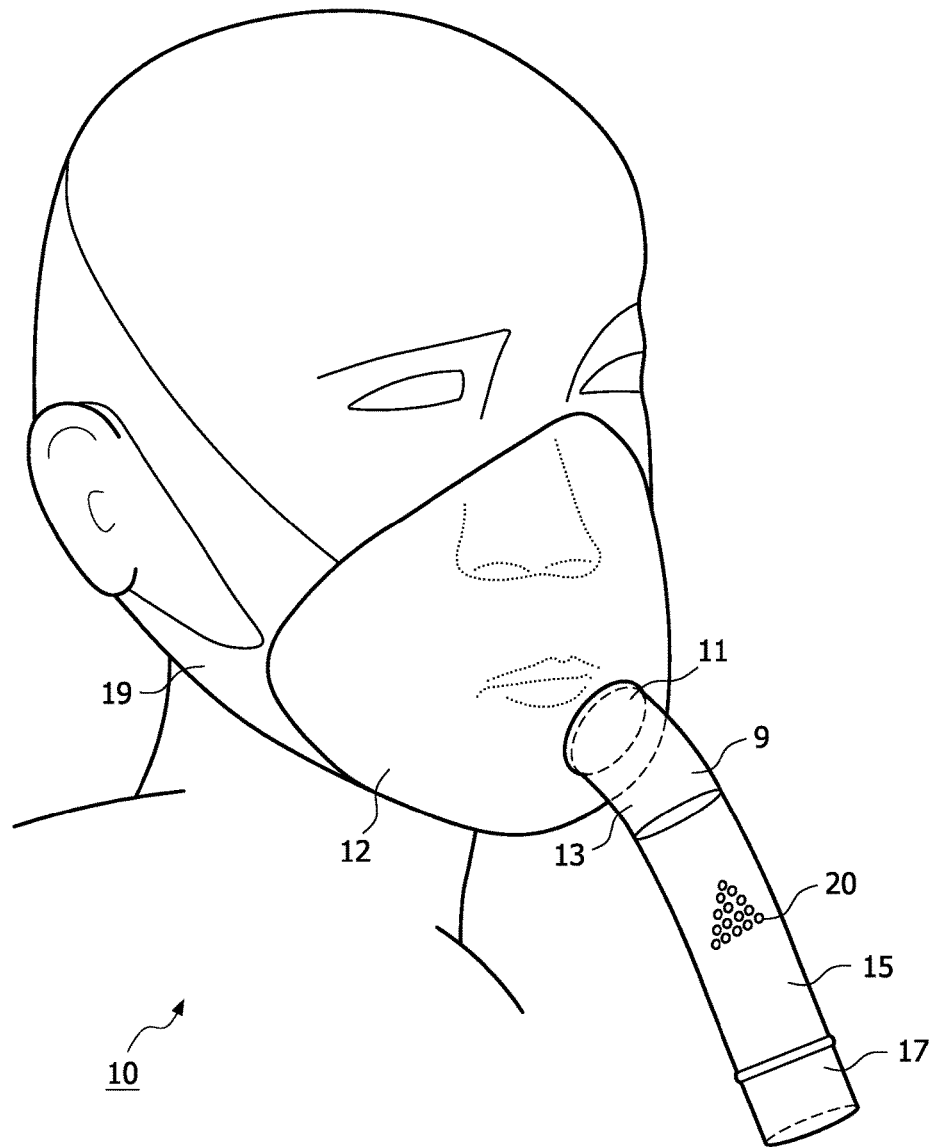
FIG. 1 is a front isometric view of a respiratory mask according to an embodiment of the invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the term "interface device" refers to any suitable mechanism for transporting gas to and/or from the airway of a user and expressly includes, but is not limited to, non-invasive interface devices such as masks (e.g., without limitation, nasal/oral masks, nasal masks, and full face masks).

As employed herein, the statement that two or more parts or components are "coupled" or "connected" together shall mean that the parts are joined or operate together either directly or through one or more intermediate parts or components.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

FIG. 1 is a front isometric view of respiratory mask 10 according to an embodiment of the invention. Respiratory mask 10 includes substantially flexible body 12 which, as shown in FIG. 1, contacts the nasal and oral portions of the user's face. Alternatively, body 12 may contact only one of the nasal portion or oral portion of the user's face. Body 12 is constructed of a fabric material. As employed herein, the term "fabric" shall mean any material that is made from weaving, knitting, crocheting, knotting, or felting fibers together. The material may be stretchable or non-stretchable; coated or uncoated. Uncoated materials preferably will be air breathable such that air may pass through the material (e.g., to allow exhaled gases to pass to the ambient atmosphere). Further, the material can include one layer or material or various layers of material, wherein the layers include the same material or various combinations of different materials. Non-limiting examples of such fabric materials include, without limitation, polyesters.

Also as shown in FIG. 1, body 12 includes opening 11 which functions as a gas inlet. Shell 13 is coupled to body 12 along the periphery of opening 11. Shell 13 is also constructed of a fabric material. Suitable fabrics for use in making shell 13 can include those described elsewhere herein for use in constructing body 12. In an embodiment, the fabric used to make shell 13 can be the same fabric as that used to make body 12. Further, in this embodiment, shell 13 can be integrally coupled to body 12. In another embodiment, the fabric used to make shell 13 can be of a different, more rigid fabric than that used to make body 12. In another particular embodiment, body 12 is made of a soft, stretchable fabric to promote comfort and shell 13 is made of a stiffer, non-stretchable but uncoated fabric to allow exhaled gases to escape to the ambient atmosphere.

Also as shown in FIG. 1, shell 13 extends outwardly from body 12 and is structured to receive therein coupling device 15. First end 9 of coupling device 15 is received into shell 13. It is contemplated that the inside diameter of shell 13 is sized such that first end 9 of coupling device 15 fits snuggly therein. In an embodiment, a fluid sealing mechanism (not shown) including, without limitation, an adhesive material, such as glue, or a flow restrictor, such as a clamp or the like, can be applied to first end 9 of coupling device 15 and/or shell 13 to enhance the seal between coupling device 15 and shell 13 and minimize or preclude leakage. Positioned opposite of first end 9 of coupling device 15 is connector end 17 which is capable of being coupled to an external gas source (not shown) through one or more conduits.

In an exemplary embodiment, connector end 17 can include a swivel connector for connecting to the one or more conduits. It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, automatic positive airway pressure (APAP) therapy and bi-level positive airway pressure (BiPAP) therapy. Coupling device 15 is employed to carry gas such as breathing air between the external gas source and mask 10. Coupling device 15 includes a venting mechanism, such as exhaust port 20, as shown in FIG. 1, for exhausting gas expired by the user to the atmosphere.

Exhaust port 20 includes a plurality of small openings that allow the exhaust gas expired by the user to exit mask 10 to the atmosphere. The particular exhaust port 20 shown in FIG. 1 is not meant to be limiting and it should be understood that the present invention contemplates a variety of different venting mechanisms that could be employed to exhaust the gas expired by the user to the atmosphere, such as, without limitation, an exhaust valve. Thus, a variety of venting mechanisms may be substituted for exhaust port 20.

Further, the particular coupling device 15 shown in FIG. 1 is not meant to be limiting and it should be understood that the present invention contemplates a variety of different coupling devices that could be received within, either permanently or selectively, shell 13 to carry gas to or from mask 10. Thus, a variety of coupling devices may be substituted for the coupling device 15.

Also, as shown in FIG. 1, mask 10 includes headgear 19 attached to body 12 to secure body 12 on each side to the user's face. Headgear 19 can be structured in a wide variety of ways to secure body 12 to the user's face and can be constructed of a wide variety of fabrics known in the art such as, without limitation, any fabric having the ability to stretch and/or flex. In the embodiment as shown in FIG. 1, headgear 19 attaches to each side of body 12 and fits around the circumference of the head of the user. Also as shown in FIG. 1, headgear 19 is integrally coupled to body 12.

Alternatively, headgear 19 can be coupled to body 12 using a wide variety of molding, bonding and fastening mechanisms such as, without limitation, sewing or stitching, snaps, straps, adhesive, and the like. In an embodiment, the same fabric can be used to construct body 12, shell 13 and headgear 19. In other embodiments, body 12 and/or shell 13 can be made of a less permeable fabric than headgear 19. In a particular embodiment, headgear 19 can be made of a more stretchable fabric than body 12. The particular headgear 19 shown in FIG. 1 is not meant to be limiting and it should be understood that the present invention contemplates a wide variety of different headgears, (e.g., adjustable or non-adjustable or combinations thereof, integrally coupled or detachably coupled) that could be employed to secure body 12 to the face of the user. Thus, a variety of headgears known in the art or hereinafter developed may be substituted for headgear 19.

Figure 2:
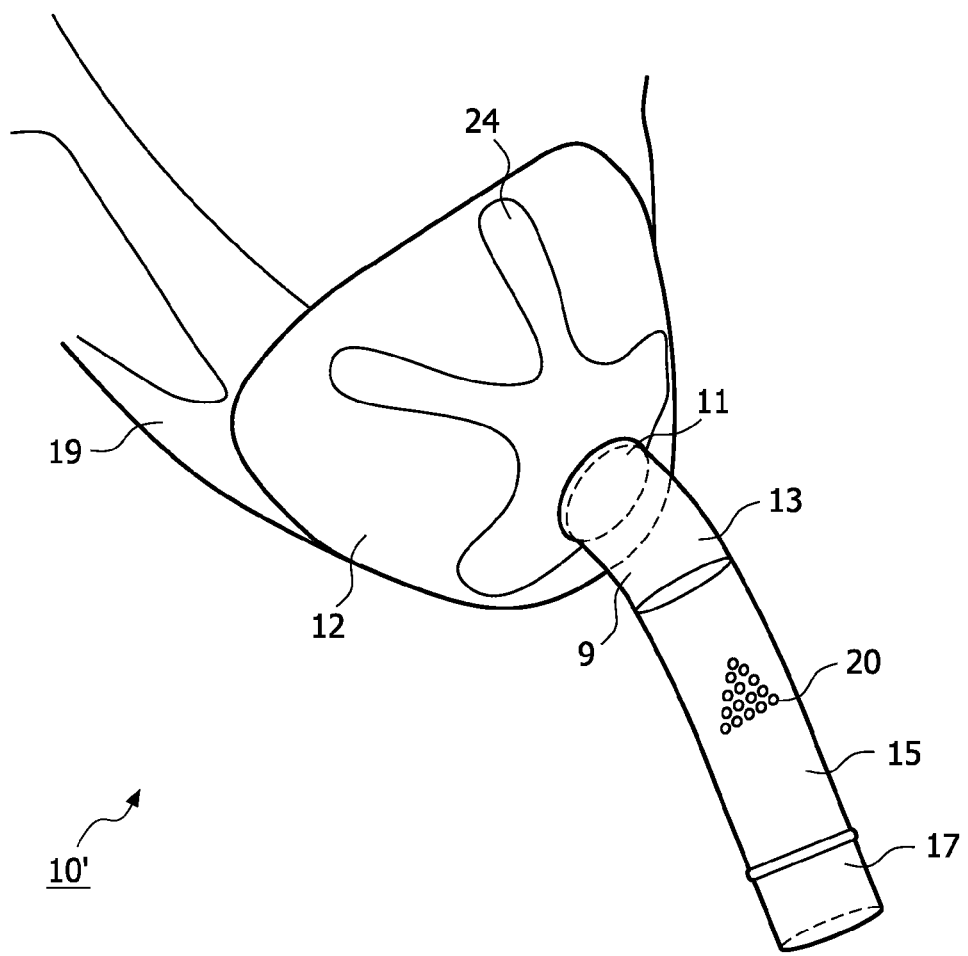
FIG. 2 is a front isometric view of a respiratory mask according to an alternative embodiment of the invention.

FIG. 2 is a front isometric view of mask 10' according to another embodiment of the invention. As shown in FIG. 2, mask 10' includes a number of the same components included as part of mask 10 in FIG. 1, including body 12, opening 11, shell 13, coupling device 15, connector end 17, exhaust port 20 and headgear 19. In addition, as shown in FIG. 2, mask 10' includes frame 21. Frame 21 is formed along the periphery of opening 11 and extends outwardly (e.g., radially) therefrom. Frame 21 can be formed on the interior surface of body 12 (e.g., the surface that comes into contact with the user's face) and/or frame 21 can be formed on the exterior surface of body 12 (as shown in FIG. 2).

Frame 21 can be formed using various molding and fastening techniques known in the art.

The exemplary frame 21, as shown in FIG. 2, is coupled to the outer surface of body 12 and is in the shape of a starfish. The particular frame 21 shown in FIG. 2 is not meant to be limiting and it should be understood that the present invention encompasses a wide variety of shapes and configurations that could be used as substitutions for frame 21. Frame 21 may be constructed of a variety of materials including, without limitation, the fabric materials described elsewhere herein for body 12 and shell 13. Frame 21 also may be constructed of a flexible, solid material, such as, without limitation, a material having greater rigidity than the materials used to make body 12 and/or shell 13 (e.g., silicone, polyurethane or foam). In an alternate embodiment, a layer of a rigid material, such as, without limitation, plastic, metal or wire can be inserted between frame 21 and the surface of body 12. It is contemplated that frame 21 in the various embodiments described will provide enhanced support to improve the effective fit of mask 10' to the user's face.

Figure 3A:
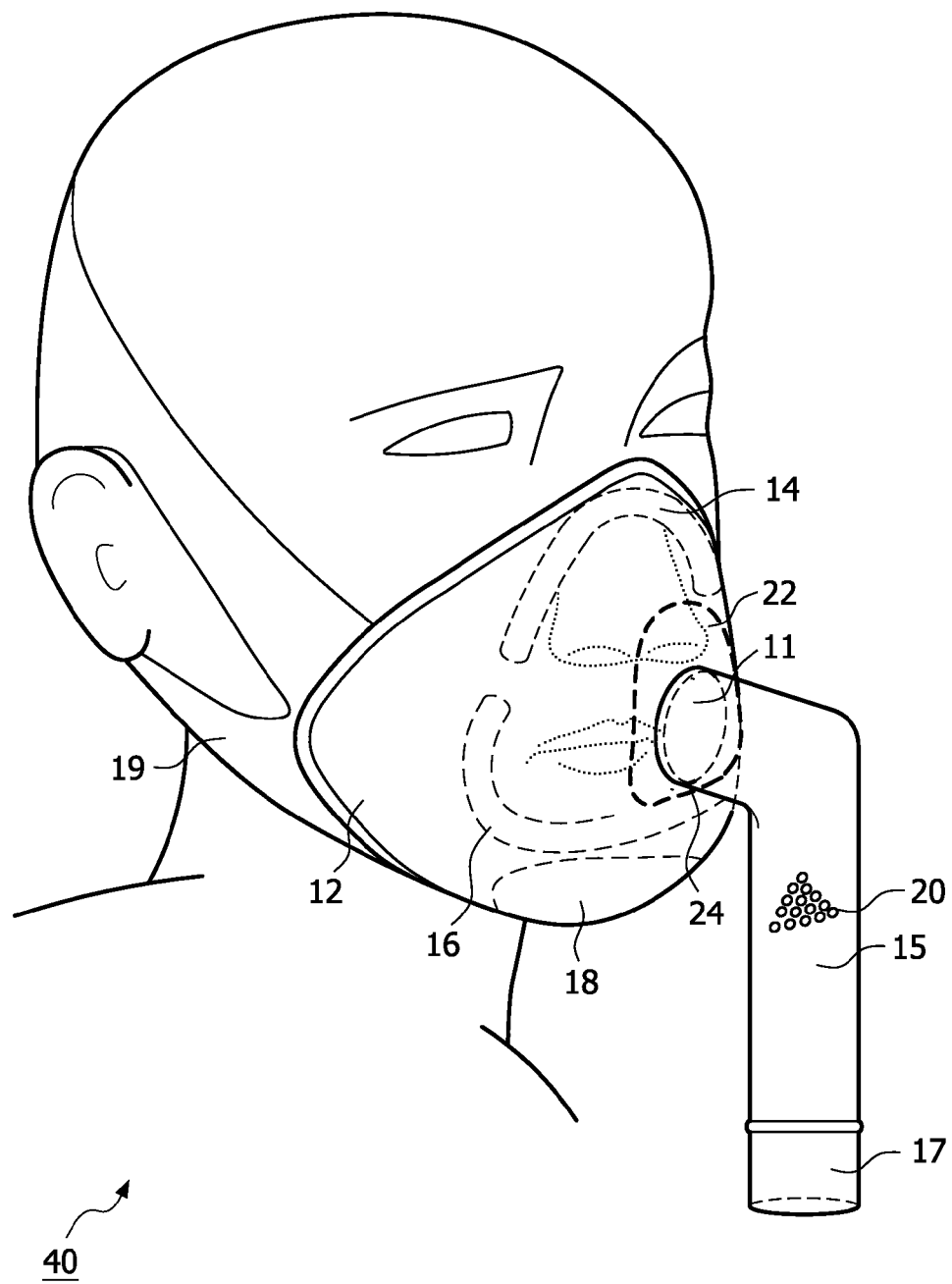
FIGS. 3a and 3b are front isometric views of a respiratory mask according to a further alternate embodiments of the invention.
Figure 3B:
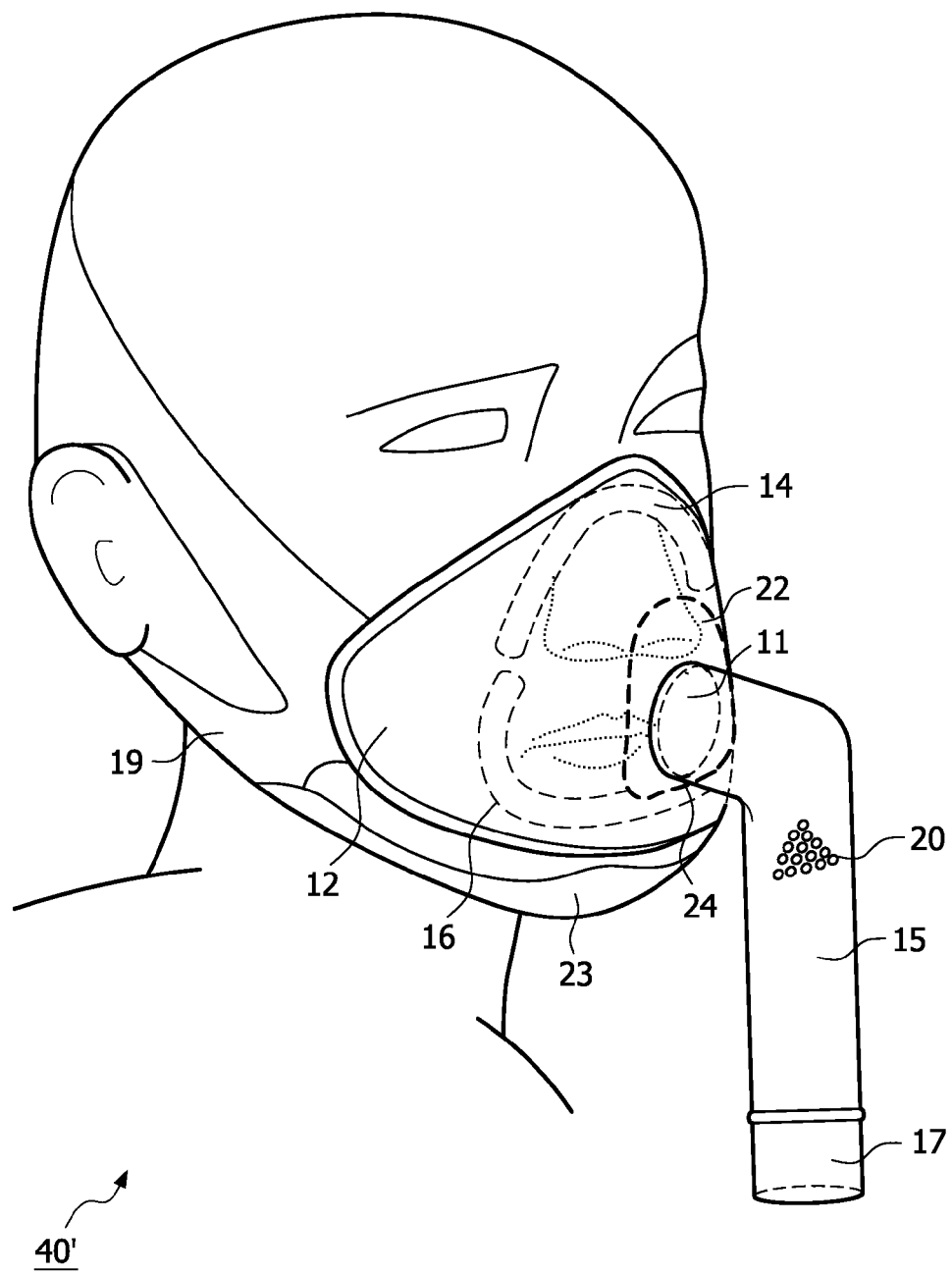

FIGS. 3a and 3b are front isometric views of masks 40 and 40' according to another embodiment of the present invention. The masks 40 and 40' are similar to masks 10 and 10' shown in FIGS. 1 and 2 and have a number of the same components such as body 12 (made of any of the fabric materials described elsewhere herein), opening 11, coupling device 15, first end 9, connector 17, exhaust port 20 and headgear 19. In addition, as shown in FIGS. 3a and 3b, the masks 40 and 40' include a nose support 14 which provides assistance in conforming and/or sealing body 12 to the contours of the nasal portion of the user's face.

As shown in FIGS. 3a and 3b, nose support 14 is positioned over the bridge of the nose of the user. The particular nose support 14 shown in FIGS. 3a and 3b is not meant to be limiting and it should be understood that a variety of shapes and configurations for the nose support are contemplated which can be substituted for nose support 14. As also shown in FIGS. 3a and 3b, nose support 14 is coupled to the interior surface of body 12. The mechanism for coupling nose support 14 to body 12 can include a wide variety of molding, bonding and fastening mechanisms known in the art such as but not limited to over-molding, gluing, stapling, or stitching. Nose support 14 can be constructed of a substantially flexible material such as a gel material, a foam material or a pad or cushion-like material.

As shown in FIGS. 3a and 3b, masks 40 and 40' also include lip support 16 coupled to body 12. Lip support 16 provides assistance in conforming and/or sealing body 12 to the contours of the oral portion of the user's face. As shown in FIGS. 3a and 3b, lip support 16 is positioned along the outer periphery of the lower lip of the user. The particular lip support 16 shown in FIGS. 3a and 3b is not meant to be limiting and it should be understood that a variety of shapes and configurations for the lip support are contemplated which can be substituted for lip support 16. As also shown in FIGS. 3a and 3b, lip support 16 is coupled to the interior surface of body 12. The mechanism for coupling lip support 16 to body 12 can include a wide variety of molding, bonding and fastening mechanisms known in the art such as but not limited to over-molding, gluing, stapling, or stitching. Lip support 16 can be constructed of a substantially flexible material such as a gel material, a foam material or a pad or cushion-like material.

The particular embodiment shown in FIG. 3a further includes a chin support, such as chin cuff 18, which provides for restricting movement of the chin of the user. Chin cuff 18 is integrally connected to the interior surface of body 12. The mechanism for connecting chin cuff 18 to body 12 can include a wide variety of molding, bonding and fastening mechanisms known in the art such as but not limited to over-molding, gluing, stapling, or stitching. Chin cuff 18 can be constructed of a substantially flexible material, such as, without limitation, silicone rubber. Further, chin cuff 18 can include a pad or cushion-like material, or a foam material. Alternatively, chin cuff 18 can be constructed of a substantially rigid material such as, without limitation, a thermoplastic material. It is contemplated that chin cuff 18 will aid in keeping closed the mouth of the user and providing an effective fit in the oral region of the user's face to prevent gapping and leaking.

The particular embodiment shown in FIG. 3b includes a chin support, such as a chin strap 23, which provides for restricting movement of the chin of the user. The exemplary chin strap 23 shown in FIG. 3b is coupled to the exterior surface of headgear 19. It is contemplated that chin strap 23 can be permanently or removably coupled to headgear 19. The mechanism for connecting chin strap 23 to headgear 19 can include a wide variety of fastening mechanisms known in the art such as but not limited to adhesive, snaps, gluing, stapling, or stitching. Chin strap 23 can be constructed of a substantially flexible material, such as, without limitation, silicone rubber. Further, chin strap 23 can include a pad or cushion-like material, or a foam material. Alternatively, chin strap 23 can be constructed of a substantially rigid material such as a thermoplastic material.

Further, as shown in FIGS. 3a and 3b, masks 40 and 40' include opening 11 which functions as a gas inlet. In the embodiment as shown in FIGS. 3a and 3b, rim 22 (preferably made of a substantially rigid material such as plastic but also possibly made of a substantially flexible (non-fabric) material as described elsewhere herein such as silicone) extends along the peripheral edge of opening 11. Rim 22 is preferably coupled to the interior surface of body 12 and provides support for connecting coupling device 15 to opening 11, for carrying gas such as breathing air between masks 40 and 40' and an external gas source (not shown). Rim 22 preferably includes a threaded mechanism which is structured to receive swivel end 24 of coupling device 15. The connector end 17 (which may or may not swivel) of coupling device 15 is coupled to an external gas source through one or more conduits such that coupling device 15 functions to transport gas from the external gas source to masks 40 and 40'.

In one particular embodiment, the thickness of rim 22 is less than the thickness of nose support 14 and lip support 16 such that rim 22 will be positioned a distance from the face of the user so that rim 22 does not come into contact with the user's face. In this embodiment, nose support 14 and lip support 16 thus also function as spacers to provide for added comfort.

Figure 4:
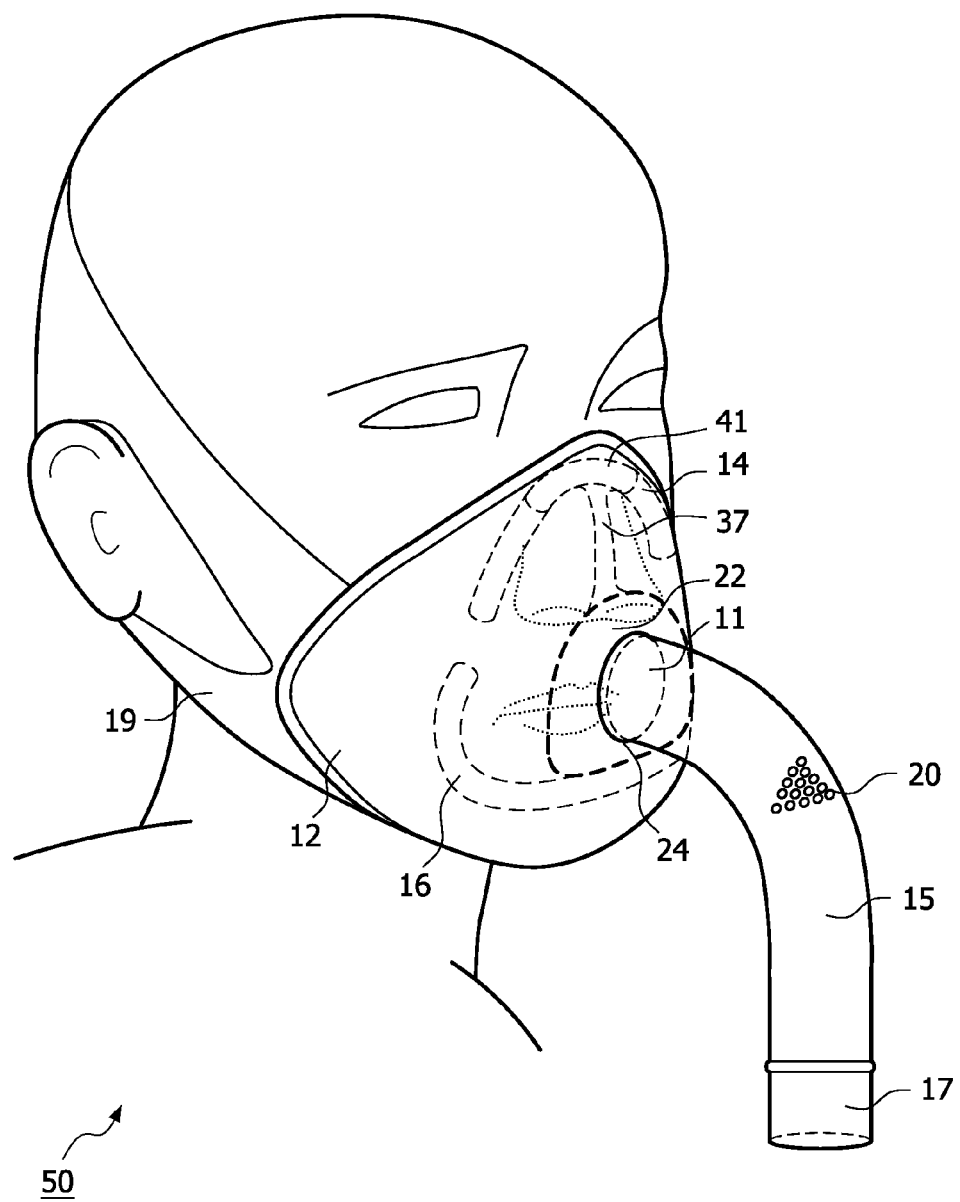
FIG. 4 is a front isometric view of a respiratory mask according to another alternate embodiment of the invention.

FIG. 4 is a front isometric view of respiratory mask 50 according to a further alternate embodiment of the invention. As seen in FIG. 4, mask 50 includes a number of the same components included as part of masks 40 and 40' in FIGS. 3a and 3b, including body 12 (made of any of the fabric materials described elsewhere herein), opening 11, nose support 14, lip support 16, rim 22, coupling device 15, swivel end 24, connector end 17, exhaust port 20 and headgear 19. In addition, as shown in FIG. 4, mask 50 includes bridge support 37 which extends upwardly from rim 22 and nose wing 41 is connected to the distal end of bridge support 37. Bridge support 37, rim 22 and nose wing 41, are preferably coupled to the interior surface (or under-side) of body 12 such that body 12 preferably forms a fabric cover over these components. In addition, nose wing 41 is preferably provided between body 12 and a portion of nose support 14.

As seen in FIG. 4, bridge support 37 is structured to engage the bridge of the user's nose in a direction along the bridge of the user's nose, and nose wing 41 is structured to engage the bridge of the user's nose in a direction substantially perpendicular to the direction of bridge support 37. In this manner, bridge support 37 and nose wing 41 provide additional support. Bridge support 37 and nose wing 41 can be constructed of various materials including, without limitation, a material that is substantially rigid, semi-rigid and/or more rigid than the fabric material used to make body 12. Suitable substantially rigid materials can include, without limitation, polymers, polyurethanes and thermoplastics.

Figure 5:
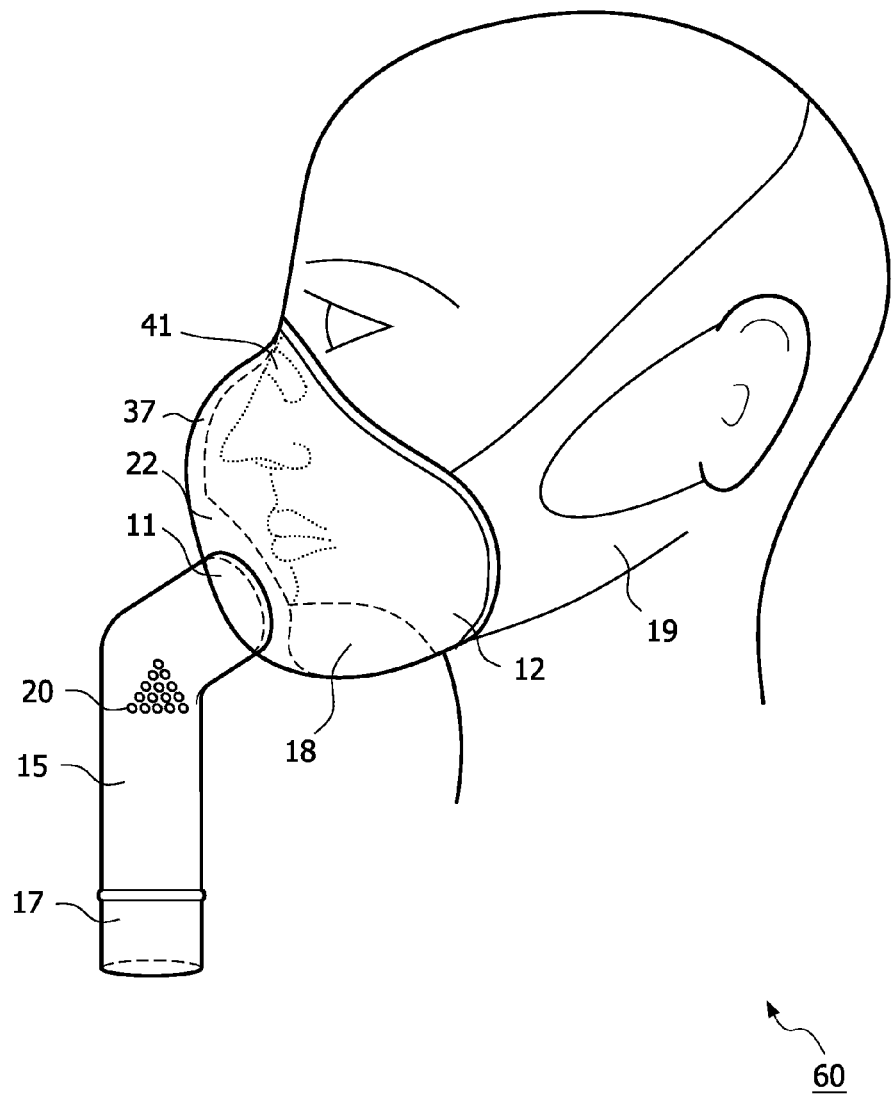
FIG. 5 is a side view of a respiratory mask according to another alternate embodiment of the invention.

FIG. 5 is a side view of respiratory mask 60 according to a further alternate embodiment of the invention. As seen in FIG. 5, mask 60 includes a number of the same components included as part of mask 50 shown in FIG. 4, including body 12, opening 11, coupling device 15, connector end 17, exhaust port 20 and headgear 19. Mask 60 does not, however, include nose support 14 and lip support 16 as shown in FIG. 4. In addition, as shown in FIG. 5, mask 60 includes rigid or semi-rigid chin cuff 18 (as previously shown in FIG. 3a and described in more detail elsewhere herein). As seen in FIG. 5, chin cuff 18 is coupled to the bottom of rim 22. As described elsewhere herein, bridge support 37 having nose wing 41 coupled thereto is coupled to the top of rim 22. As a result of chin cuff 18 engaging the user's chin (as described elsewhere herein) and bridge support 37 and nose wing 41 engaging the user's nose (as described elsewhere herein), rim 22 and a portion of bridge support 37 will be positioned a distance from the user's face for added comfort.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. A respiratory interface device, comprising:
a fabric body structured to accommodate one or both of a nasal and oral region of a user's face, the fabric body having a rear portion, which is structured to contact the user's face, and a front portion, the rear portion defining a first opening structured to surround a portion of the user's face, the front portion having a second opening formed therein;
a tubular fabric connecting member having a first end and an opposite second end, extending outwardly from the front portion of the fabric body in a direction away from the user's face, the first end of the fabric connecting member being coupled to the fabric body and extending along a periphery of the second opening to form an interior cavity within the fabric connecting member having an inside surface and an inside diameter; and
a coupling device for delivering a gas to the respiratory interface device, the coupling device having a first end, a second end, an outside diameter and an exterior surface, the first end of the coupling device being inserted into the second end of the fabric connecting member, the inside diameter of the fabric connecting member and the outside diameter of the coupling device being sized such that the first end of the coupling device fits snuggly in at least a portion of the interior cavity of the fabric connecting member, said coupling device being removably fitted within the fabric connecting member, and the second end of the coupling device being coupled to an external gas source to supply gas for consumption by the user,
wherein, the inside surface of the second end of the fabric connecting member is structured to extend outwardly over the exterior surface of the outside diameter of the first end of the coupling device, and
wherein, the fabric body is constructed of a first fabric material and the tubular fabric connecting member is constructed of a second fabric material, the second fabric material being more rigid than the first fabric material.

2. The respiratory interface device according to claim 1, wherein the first fabric material is stretchable and wherein the second fabric material is non-stretchable and breathable.

3. A respiratory interface device, comprising:
a fabric body structured to accommodate one or both of a nasal and oral region of a user's face, the fabric body having a rear portion, which is structured to contact the user's face, and a front portion, the rear portion defining a first opening structured to surround a portion of the user's face, the front portion having a second opening formed therein;
a flexible frame coupled to a surface of the fabric body, the flexible frame extending along the periphery of the second opening and extending outwardly therefrom;
a tubular fabric connecting member having a first end and an opposite second end, extending outwardly from the front portion of the fabric body in a direction away from the user's face, the first end of the fabric connecting member being coupled to the fabric body and extending along a periphery of the second opening to form an interior cavity within the fabric connecting member having an inside surface and an inside diameter; and
a coupling device for delivering a gas to the respiratory interface device, the coupling device having a first end, a second end, an outside diameter and an exterior surface, the first end of the coupling device being inserted into the second end of the fabric connecting member, the inside diameter of the fabric connecting member and the outside diameter of the coupling device being sized such that the first end of the coupling device fits snuggly in at least a portion of the interior cavity of the fabric connecting member, said coupling device being removably fitted within the fabric connecting member, and the second end of the coupling device being coupled to an external gas source to supply gas for consumption by the user,
wherein, the inside surface of the second end of the tubular fabric connecting member is structured to extend outwardly over the exterior surface of the outside diameter of the first end of the coupling device, and
wherein, the fabric body is made of a first fabric material and wherein the tubular fabric connecting member and the flexible frame are made of a second fabric material, the second fabric material being more rigid than the first fabric material.

4. A respiratory interface device, comprising:
a fabric body structured to accommodate one or both of a nasal and oral region of a user's face, the fabric body having an interior surface structured to be in contact with the user's face and an opening formed therein;

a coupling device having a swivel end for delivering a gas to the respiratory interface device;

a rim coupled to the interior surface of the fabric body and structured to extend around a perimeter of the opening, the rim having a threaded mechanism structured to connect to the swivel end of the coupling device;

a nose support element having a thickness and being structured to engage a nose of the user's face, the nose support element constructed of a substantially flexible material, coupled to the interior surface of the fabric body, and extending outwardly from the interior surface of the fabric body in a direction toward the user's face; and a lip support element having a thickness and being structured to engage the user's face immediately below a mouth of the user's face, the lip support element constructed of a substantially flexible material, coupled to the interior surface of the fabric body, and extending outwardly from the interior surface of the fabric body in a direction toward the user's face, wherein, the thickness of each of the nose support element and the lip support element is effective to space apart the rim from the user's face.

5. The respiratory interface device of claim 4, wherein the nose support element is constructed of a material selected from the group consisting of gel, foam, pad and cushion.

6. The respiratory interface device of claim 4, wherein the lip support element is constructed of a material selected from the group consisting of gel, foam, pad and cushion.

7. The respiratory interface device of claim 4, further comprising a bridge support element having a bridge support portion coupled to and extending from the rim and structured to engage a bridge of the user's nose along a first direction, the bridge support element further having a nose wing portion coupled to the bridge support portion for engaging the bridge of the user's nose along a second direction substantially perpendicular to the first direction.

8. The respiratory interface device of claim 4, wherein the nose support element and the lip support element are coupled to the fabric body using a mechanism selected from the group consisting of over-molding, gluing, stapling and stitching.

9. The respiratory interface device of claim 8, wherein a thickness of the rim is less than a thickness of each of the nose support element and the lip support element.

10. The respiratory interface device of claim 8, further comprising a non-fabric chin support element coupled to the fabric body, the chin support element being structured to engage a chin portion of the user's face.

11. The respiratory interface device of claim 4, further comprising a chin support element coupled to the fabric body, the chin support element being structured to engage a chin portion of the user's face, the chin support element being coupled to the rim for spacing the rim from a face of the user.

12. The respiratory interface device of claim 11, further comprising a bridge support element coupled to the fabric body, the bridge support element having a bridge support portion coupled to and extending from the rim and structured to engage a bridge of a user's nose along a first direction, the bridge support element further having a nose wing portion coupled to the bridge support portion for engaging the bridge of the user's nose along a second direction substantially perpendicular to the first direction.

* * * * *